US008721652B2

(12) United States Patent
Hawkins et al.

(10) Patent No.: US 8,721,652 B2
(45) Date of Patent: May 13, 2014

(54) VOLUME MEASURING INTERVERTEBRAL TOOL SYSTEM AND METHOD

(71) Applicant: DePuy Synthes Products, LLC, Raynham, MA (US)

(72) Inventors: John Riley Hawkins, Cumberland, RI (US); Michael J. O'Neil, West Barnstable, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/787,297

(22) Filed: Mar. 6, 2013

(65) Prior Publication Data

US 2013/0184710 A1  Jul. 18, 2013

Related U.S. Application Data

(62) Division of application No. 11/726,954, filed on Mar. 23, 2007, now Pat. No. 8,398,640.

(51) Int. Cl.
*A61B 17/14* (2006.01)
*A61B 17/56* (2006.01)

(52) U.S. Cl.
USPC ............................................. 606/102; 606/82

(58) Field of Classification Search
USPC ......... 606/79, 80, 82–85, 102, 128, 159, 167, 606/168, 170, 172, 173, 176–178, 180; 30/381, 385, 386; 83/830, 832
See application file for complete search history.

(56) References Cited

U.S. PATENT DOCUMENTS

| 5,269,797 | A | 12/1993 | Bonati et al. |
| 5,725,530 | A | 3/1998 | Popken |
| 6,415,516 | B1 | 7/2002 | Tirado et al. |
| 6,969,404 | B2 * | 11/2005 | Ferree ........................ 623/17.11 |
| 7,686,770 | B2 | 3/2010 | Cohen |
| 7,918,849 | B2 | 4/2011 | Bleich et al. |
| 8,021,379 | B2 | 9/2011 | Thompson et al. |
| 8,021,380 | B2 | 9/2011 | Thompson et al. |
| 8,167,883 | B2 | 5/2012 | Termanini |
| 8,241,282 | B2 | 8/2012 | Unger et al. |
| 2002/0053270 | A1 | 5/2002 | King |
| 2004/0148788 | A1 | 8/2004 | Behbahany |
| 2005/0028378 | A1 | 2/2005 | Stones et al. |
| 2005/0033292 | A1 | 2/2005 | Teitelbaum et al. |
| 2005/0090809 | A1 | 4/2005 | Cooper et al. |
| 2005/0273111 | A1 | 12/2005 | Ferree et al. |
| 2006/0030854 | A1 | 2/2006 | Haines |
| 2006/0094976 | A1 | 5/2006 | Bleich |
| 2006/0100651 | A1 | 5/2006 | Bleich |
| 2006/0195017 | A1 * | 8/2006 | Shluzas et al. ................ 600/210 |

(Continued)

FOREIGN PATENT DOCUMENTS

EP    1101471  A2   5/2001
WO   WO03001986     1/2003

*Primary Examiner* — Michael T Schaper
(74) *Attorney, Agent, or Firm* — Maginot, Moore & Beck LLP

(57) ABSTRACT

The invention includes a system and method for the loosening of tissue. In one embodiment, a method of removing intervertebral tissue includes removing tissue with a loosening member to form a void, inserting a portion of the loosening member into the void, and determining the amount of tissue removed based upon the volume defined by the portion of the loosening member inserted into the void.

20 Claims, 10 Drawing Sheets

(56) References Cited

U.S. PATENT DOCUMENTS

| | | |
|---|---|---|
| 2006/0241566 A1 | 10/2006 | Moon et al. |
| 2006/0247657 A1* | 11/2006 | Trieu .......................... 606/102 |
| 2006/0282065 A1 | 12/2006 | Cohen |
| 2007/0100361 A1 | 5/2007 | Cohen |
| 2008/0009876 A1* | 1/2008 | Sankaran et al. ............... 606/84 |
| 2008/0033443 A1 | 2/2008 | Sikora et al. |
| 2008/0319442 A1 | 12/2008 | Unger et al. |

* cited by examiner

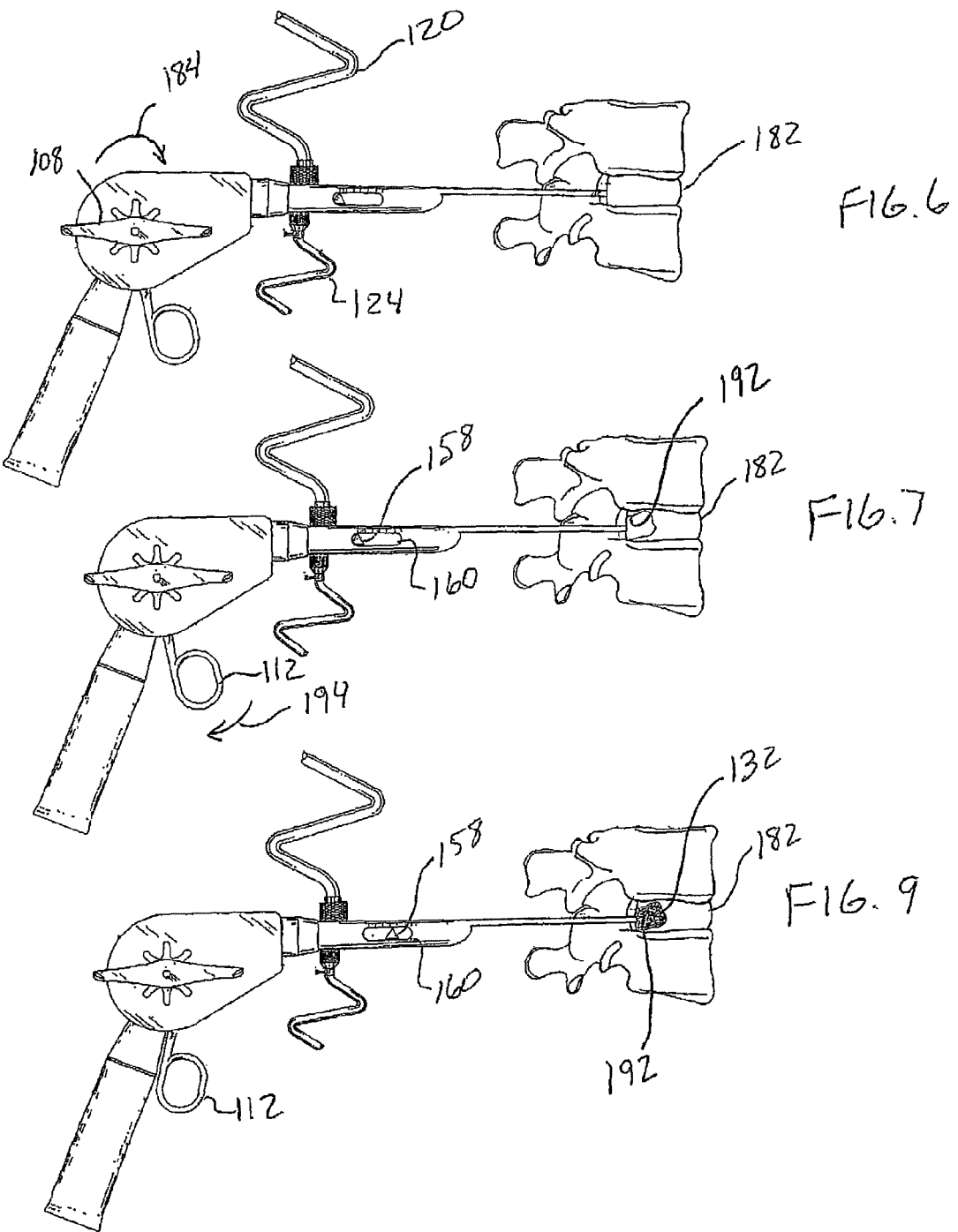

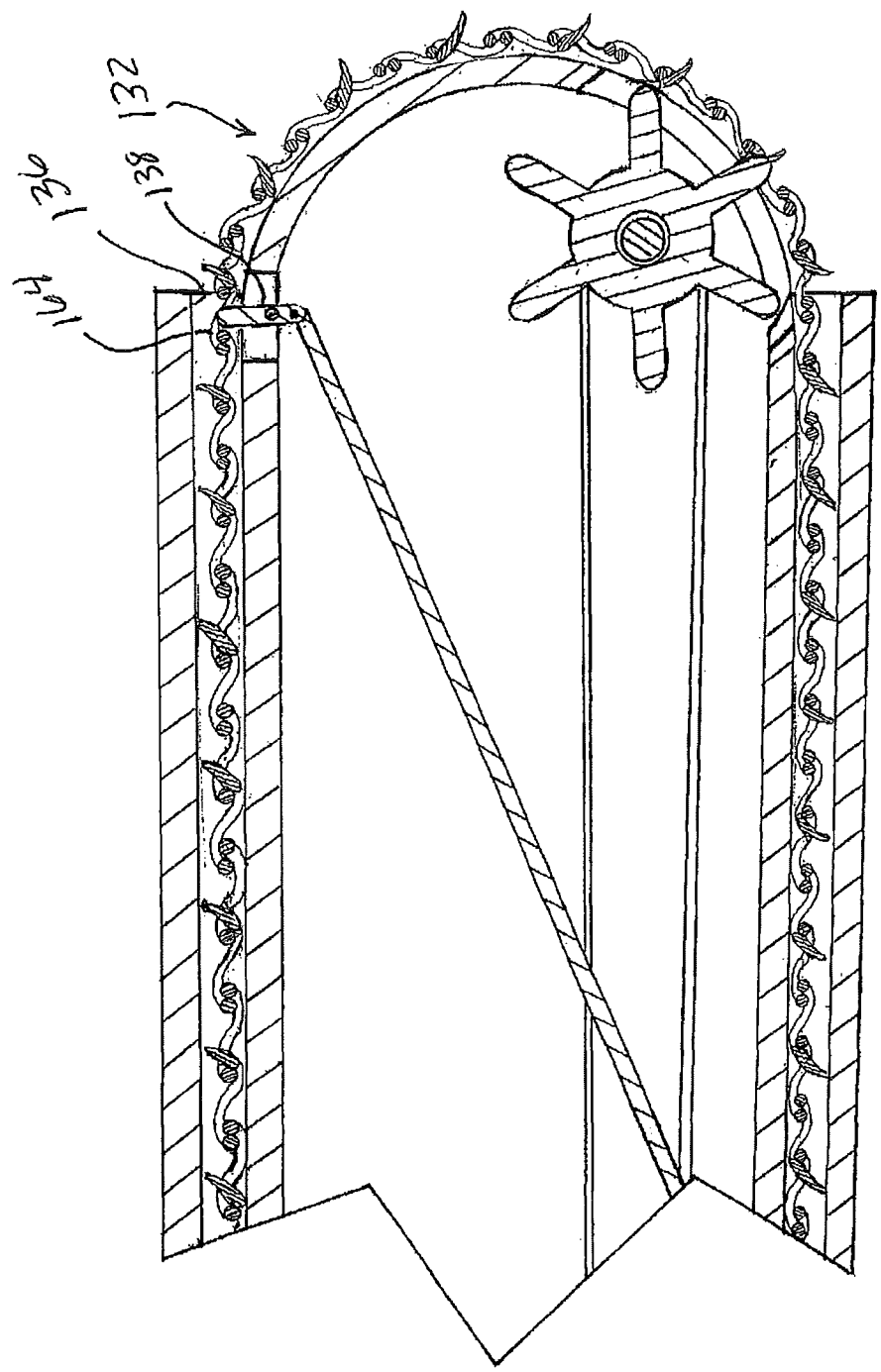

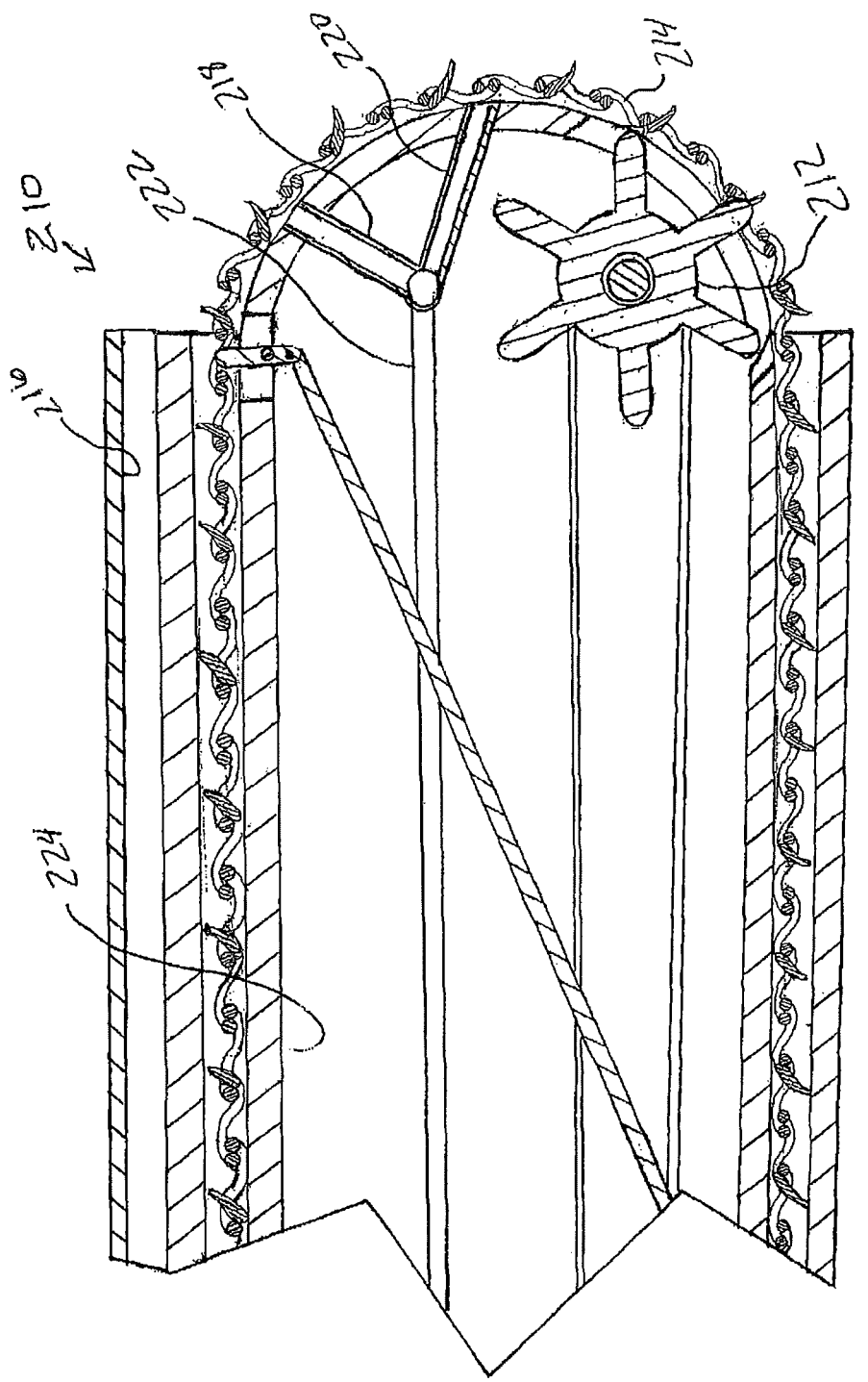

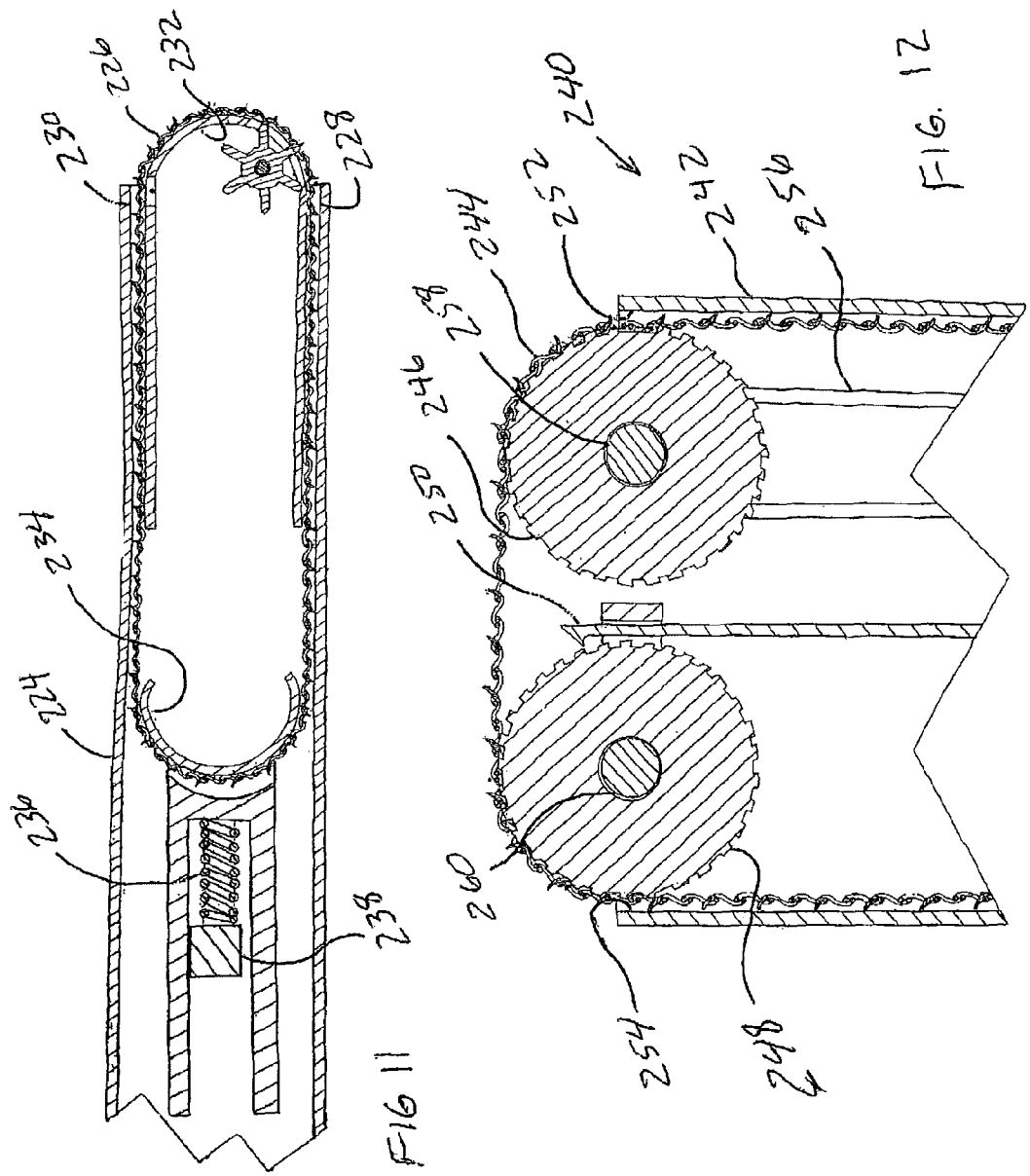

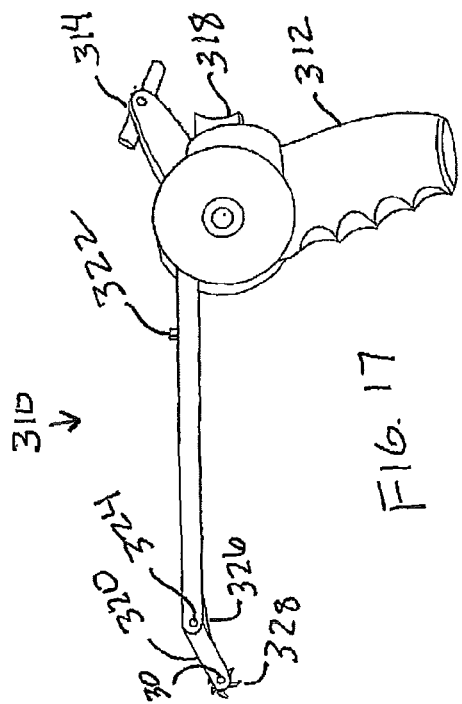
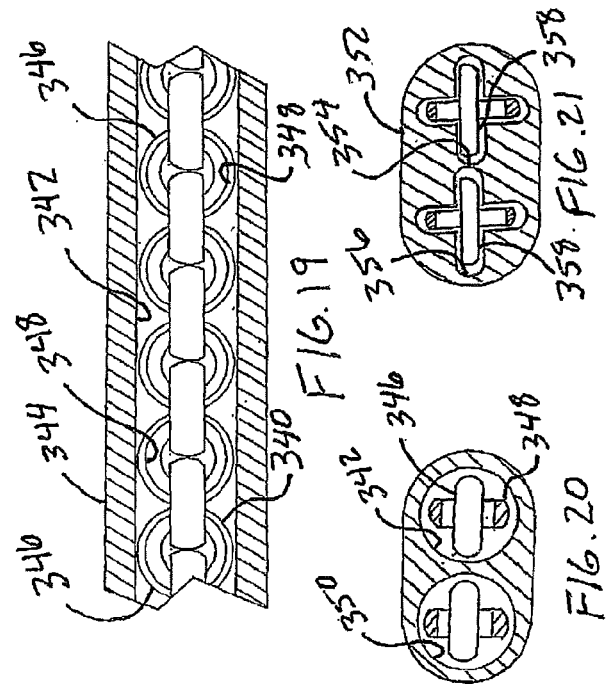
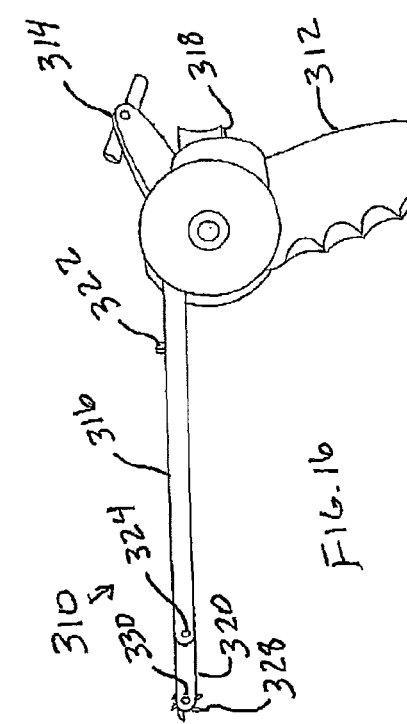
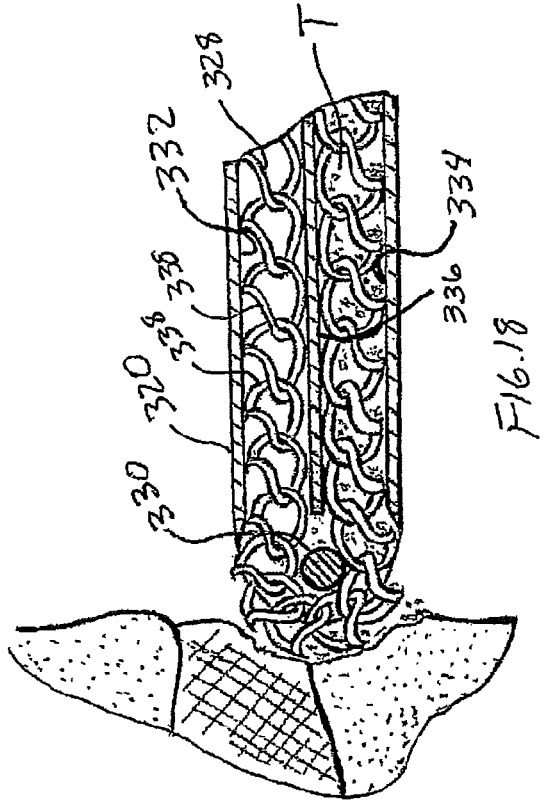

VOLUME MEASURING INTERVERTEBRAL TOOL SYSTEM AND METHOD

This application is a divisional of U.S. application Ser. No. 11/726,954, filed Mar. 23, 2007 (now U.S. Pat. No. 8,398,640 issued in Mar. 19, 2013), the disclosure of which is hereby totally incorporated by reference in its entirety.

FIELD OF THE INVENTION

This invention relates to surgical devices and, more particularly, to devices used to loosen tissue for removal in a surgical patient.

BACKGROUND

The spinal column acts as a major structural support. Various mechanisms, however, affect the ability of intervertebral disks to provide the requisite stability and support. For example, the normal aging process tends to weaken the bones and tissues associated with the spinal column increasing the risk of spinal injuries. Additionally, sudden movements may cause a disk to rupture or herniate. A herniation of the disk is primarily a problem when the nucleus pulposus protrudes or ruptures into the spinal canal placing pressure on nerves which in turn causes spasms, tingling, numbness, and/or pain in one or more parts of the body, depending on the nerves involved. Further deterioration of the disk can cause the damaged disk to lose height and to produce bone spurs. These mechanisms may result in a narrowing of the spinal canal and foramen, thereby causing undesired pressure on the nerves emanating from the spinal cord.

Treatments of spinal cord conditions include various procedures which involve the removal of all or a portion of a spinal component. Such procedures may include the injection of an enzyme into an affected disk to dissolve tissues. The enzymes typically used in this procedure are protein-digesting enzymes which must be carefully placed with respect to the spinal defect to avoid inadvertent dissolution of spinal tissue.

Alternatively, surgical access to a spinal area may be obtained and a tool such as a curette, osteotome, reamer, rasp, or drill may be used to mechanically reshape a component of the spinal column. The tissue removed may include disk tissue which is causing pressure on a nerve or the spinal canal. This technique is highly invasive and traumatic to the body, and therefore requires an extended recovery period. Moreover, there are increased risks of future problems due to the removal of a portion of the lamina which is no longer in place to support and protect the spinal canal at the area where the surgery took place.

Surgical access may also be used for spinal fusion surgery. In a fusion procedure, a damaged disk may be completely removed. Parts of a bone from another part of the patient's body, such as the pelvis, are harvested, and the bone parts or grafts are subsequently placed between the adjacent vertebrae so that the adjacent vertebrae grow together in a solid mass. The recovery time for a normal spinal fusion surgery is significant due not only to the fact that normal movement cannot be allowed until detectable bone growth has occurred between the bone grafts and the adjacent vertebrae, but also due to the fact that the associated ligaments and muscles, both at the spinal location and the location where the bone grafts were harvested, must also recover.

Recently, efforts have been directed to replacing defective spinal column components. When this type of procedure is performed in a minimally invasive manner, it is known for various devices implanted during the procedure to be subsequently expelled from the intervertebral disks. This expulsion is frequently attributed to inadequate clearance of the nucleus during the minimally invasive surgical procedure. The result is that the interdiskal device extrudes from the cavity formed in the spinal column, increasing the potential for expulsion.

A need exists for a device for loosening tissue that is minimally invasive, easy to use, and safe. A further need exists for a device which provides for both the loosening of tissue and the removal of loosened tissue. A further need exists for a device which can be used to determine the amount of loosened tissue that has been removed.

SUMMARY

A system and method for loosening of tissue is disclosed. In accordance with one embodiment according to the invention a method of removing intervertebral tissue includes removing tissue with a loosening member to form a void, inserting a portion of the loosening member into the void, and determining the amount of tissue removed based upon the volume defined by the portion of the loosening member inserted into the void.

In accordance with another embodiment, an intervertebral tissue removal system includes a cannula having a first end portion for insertion into tissue, a feed passage within the cannula, a return passage within the cannula, and a loosening member movable within the feed passage and the return passage and at least partially deployable away from the first end portion of the cannula.

In accordance with a further embodiment, a tissue loosening device includes a cannula, a loosening member extending outwardly of the cannula, a moving member operably engaged with the loosening member for moving the loosening member, and a locking member movable between a first position, wherein the locking member restricts movement of the loosening member and a second position wherein the locking member allows movement of the loosening member. The locking member configured such that when the locking member is in the first position and the loosening member is moved by the moving member the loosening member is deployed from the cannula, and when the locking member is in the second position and the loosening member is moved by the moving member the loosening member is rotated about a loop path.

The above-described features and advantages, as well as others, will become more readily apparent to those of ordinary skill in the art by reference to the following detailed description and accompanying drawings.

BRIEF DESCRIPTION OF THE DRAWINGS

FIG. 6 depicts a partial schematic view of the intervertebral tissue removal system of FIG. 1 with the cannula positioned partially within a disc;

FIG. 7 depicts a partial schematic view of the intervertebral tissue removal system of FIG. 1 with the cannula positioned partially within a disc which has a void formed therein;

FIG. 8 depicts a partial cross-sectional view of the cannula of FIG. 1 with the locking member engaged with the loosening member;

FIG. 9 depicts a partial schematic view of the intervertebral tissue removal system of FIG. 1 with the cannula positioned partially within a disc with a portion of the loosening member deployed from the cannula to measure the volume of the void formed in the disc;

FIG. 10 depicts a partial cross-sectional view of an alternative embodiment of a cannula with aspiration branches provided through the loosening track of the cannula in accordance with principles of the present invention;

FIG. 11 depicts a partial cross-sectional view of an alternative embodiment of a cannula with a biasing member that is located outside of the loop path and which biases a tensioning track away from a loosening track in accordance with principles of the present invention;

FIG. 12 depicts a partial cross-sectional view of an alternative embodiment of a cannula with a loop path formed by a freewheeling member and a moving member;

FIG. 16 depicts a side perspective view of an alternative intervertebral tissue removal device with a crank handle, a clutch control, a brake lever and a cannula with a pivoting tip incorporating principles of the present invention;

FIG. 17 depicts a side perspective view of the tissue removal device of FIG. 16 with the pivoting tip of the canula pivoted with respect to the position of the pivoting tip in FIG. 16;

FIG. 18 depicts a partial side cross-sectional view of the pivoting tip of the device of FIG. 16 with a perspective view of the loosening member showing the loosening member extending within passages in the cannula and around a bearing with a diameter larger than the width of the divider between the passages;

FIG. 19 depicts a partial side cross-sectional view of an alternative tissue removal device with a perspective view of a loosening member showing the loosening member extending within passages in the cannula incorporating principles of the present invention;

FIG. 20 depicts a partial end cross-sectional view of the tissue removal device of FIG. 19 with a perspective view of the loosening member showing the footprint of the loosening member within the cross-sections of the passages; and FIG. 21 depicts a partial end cross-sectional view of an alternative tissue removal device with a perspective view of the loosening member showing the footprint of the loosening member within the shaped cross-sections of the passages.

DETAILED DESCRIPTION

Figure 1:
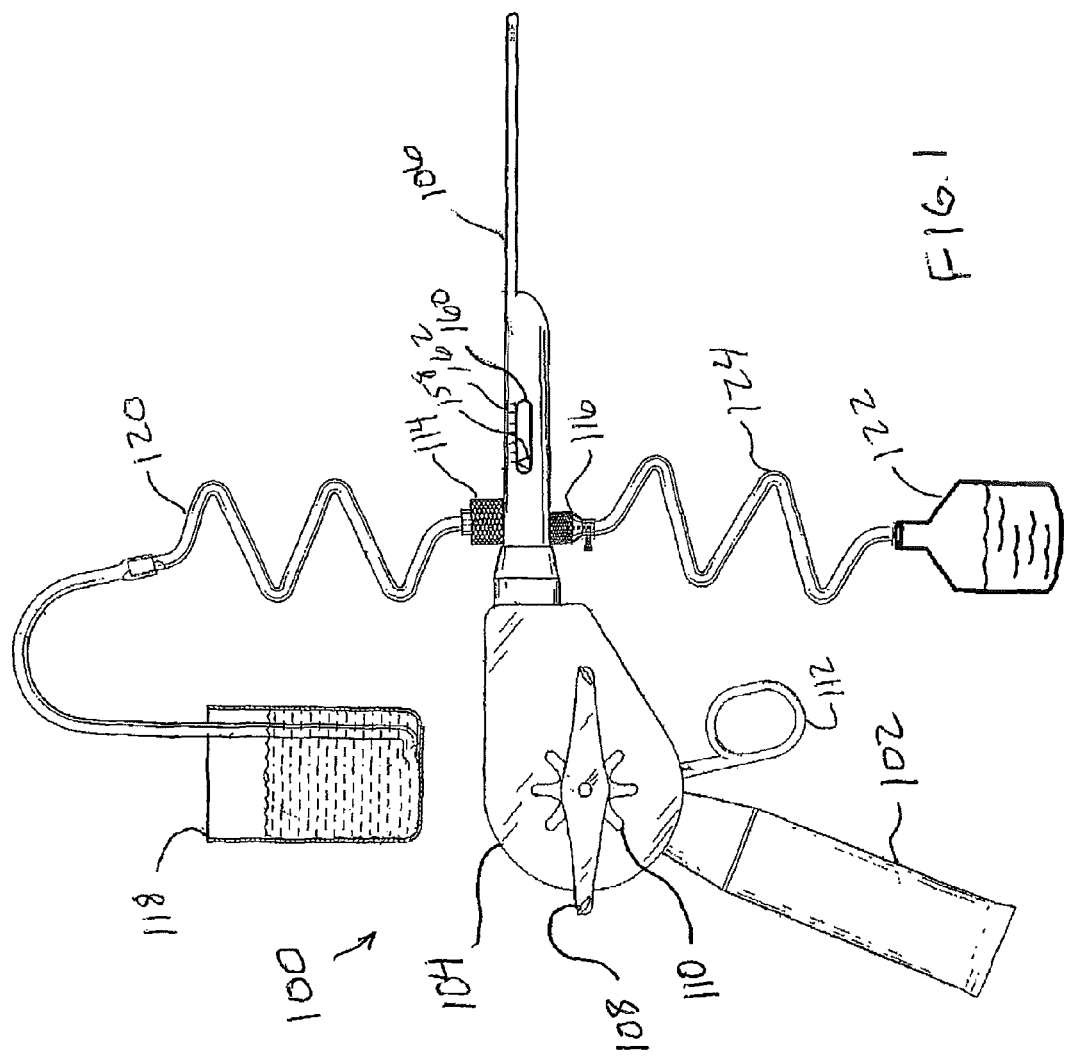
FIG. 1 depicts a schematic view of an intervertebral tissue removal system with a crank handle, a clutch control, a brake lever and a cannula incorporating principles of the present invention.

FIG. 1 depicts an intervertebral tissue loosening device 100 which includes a grip 102, a main housing 104 and cannula 106. A crank handle 108, a clutch 110 and a brake lever 112 extend from the main housing 104. An aspiration port 114 and an outlet port 116 are provided on the cannula 106. The cannula 106 preferably has a diameter of between about 3 millimeters to about 10 millimeters.

A fluid reservoir 118 is in fluid connection with the cannula 106 through a tube 120 which is connected to the aspiration port 114. In this embodiment, the fluid reservoir 118 is configured to provide a liquid in the form of saline solution under pressure to the aspiration port 114. The fluid may be pressurized in a number of acceptable ways such as using a gas to pressurize the fluid reservoir 118 or a pump that takes suction from the fluid reservoir 118.

The outlet port 116 is in fluid connection with a collector 122 through a tube 124. In alternative embodiments, the collector 122 may be replaced with a vacuum collection system so as to provide a suction source for the cannula 106 through the outlet port 116. Additionally, the tube 124 may be directed to waste if so desired.

Figure 2:
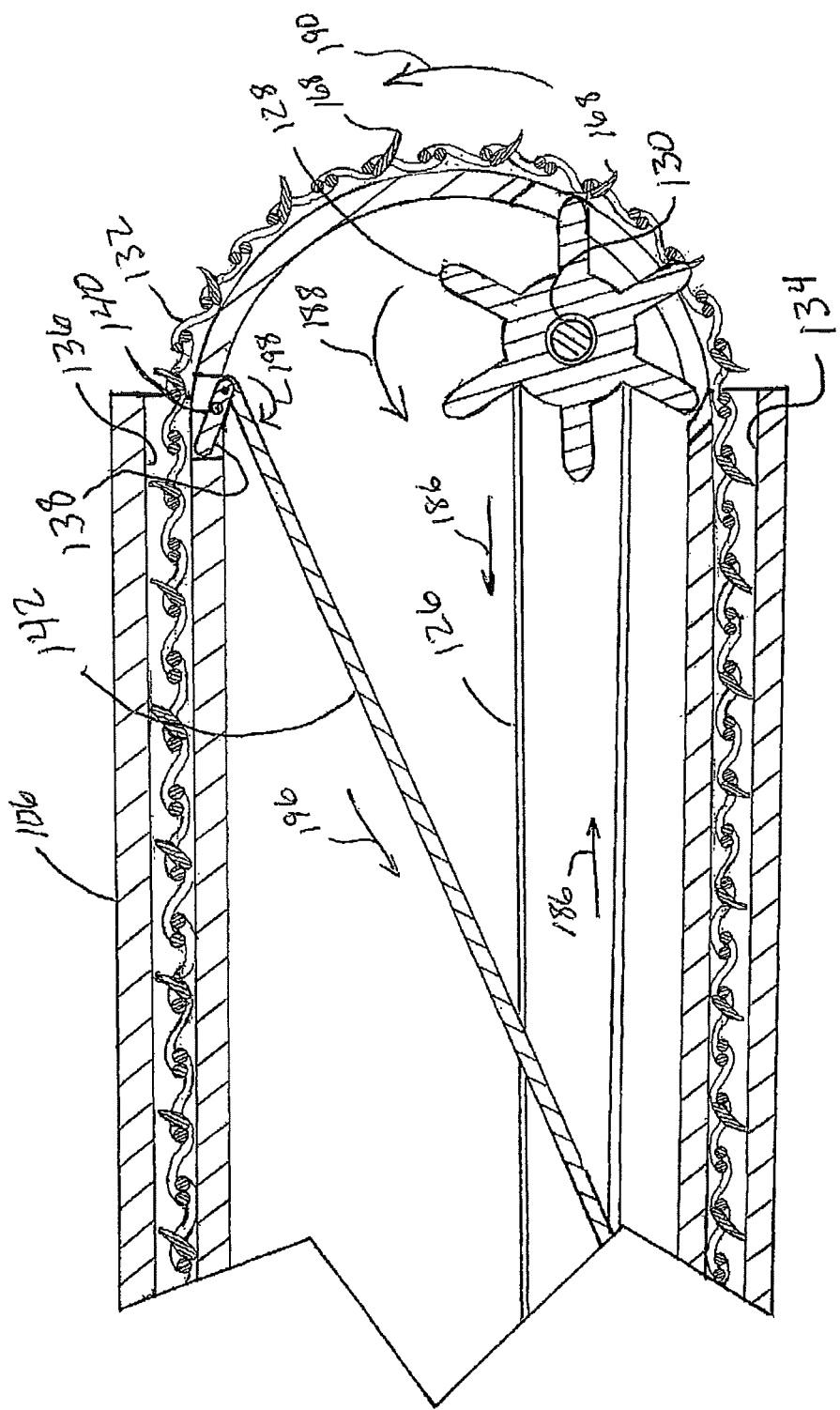
FIG. 2 depicts a partial cross-sectional view of a moving member, a locking member and a continuous loop loosening member within a feed passage and return passage of the cannula of FIG. 1.

The crank handle 108 is operably connected to a belt 126 which extends into the cannula 106 as best seen in FIG. 2. The belt 126 is operably connected to a sprocket 128 which is rotatably mounted on a pin 130. The sprocket 128 is engaged with a chain 132 formed in a continuous loop which extends along a feed passage 134, a loosening track 135 and a return passage 136 of the cannula 106. The chain 132 preferably has a diameter in the range of about 1 millimeter to about 3 millimeters. Also shown in FIG. 2 is a locking member 138 which is pivotably mounted to the cannula 106 by a pin 140. A connector arm 142 is pivotably connected to the locking member 138 and operably connected to the brake lever 112.

Figure 3:
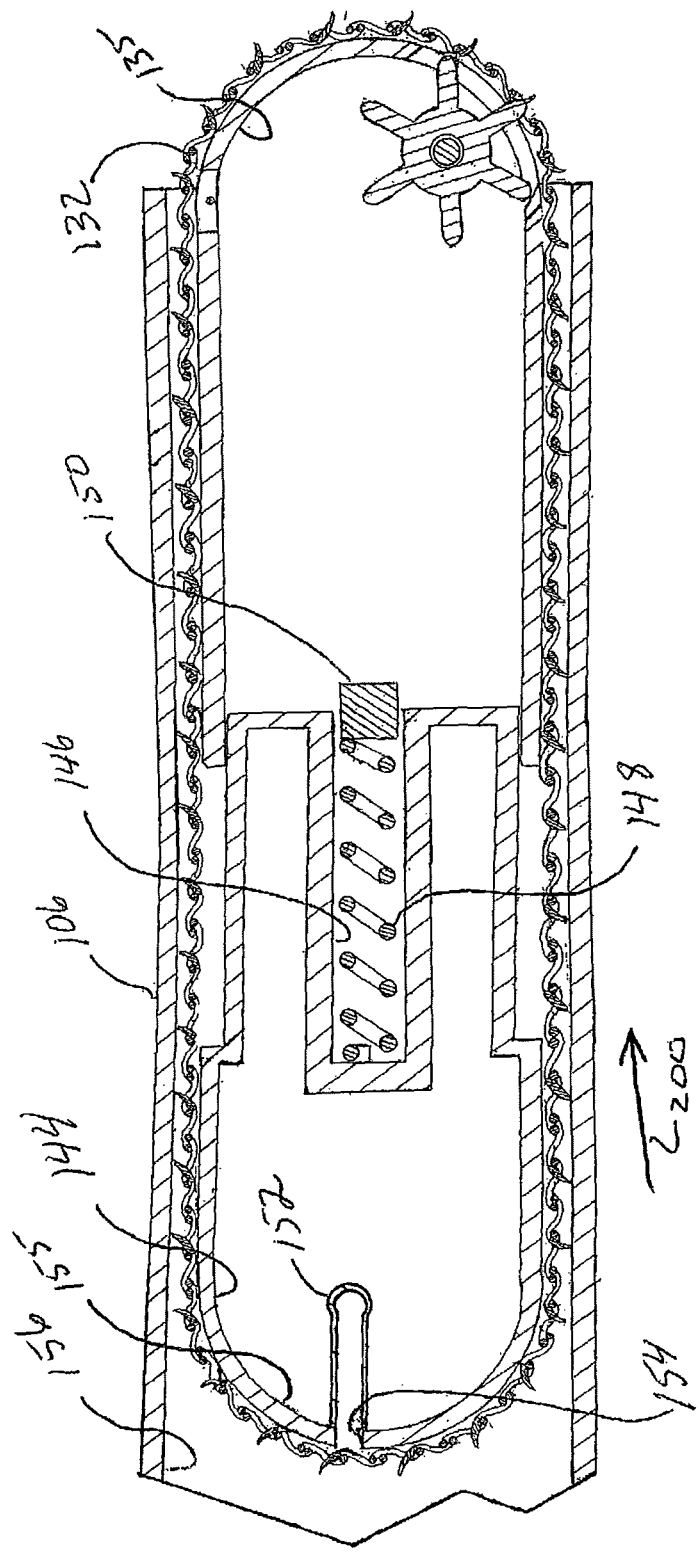
FIG. 3 depicts a partial cross-sectional view of the cannula of FIG. 1 with a biasing member acting upon a tensioning member to keep the loosening member of FIG. 2 taut completely about the loop path.

Continuing with FIG. 3, the chain 132 extends around a tensioning portion 144 that is located within the cannula 106. The tensioning portion 144 includes a blind bore 146 which receives a biasing member 148. The biasing member 148, which is configured to provide a relatively constant biasing force as it is compressed, is maintained within the blind bore 146 by a stop 150 which is fixedly connected to the cannula 106. A tube 152 is in fluid communication with the aspiration port 114 at one end.

The other end of the tube 152 is in fluid communication with an evacuation chamber 156 through an opening 154 in a tensioning track 155 of the tensioning portion 144. The evacuation chamber 156 is in fluid communication with the outlet port 116. An indicator 158 is connected to the tensioning portion 144 and is visible through a sight glass 160 shown in FIG. 1. A plurality of gradations 162 are located on the cannula 106 adjacent to the sight glass 160.

Figure 4:
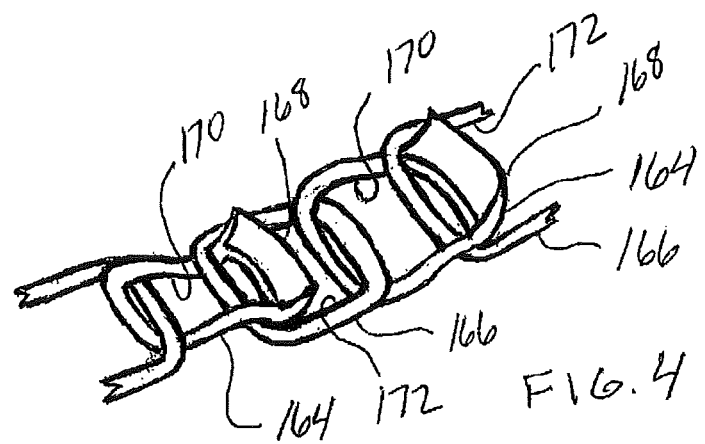
FIG. 4 depicts a partial perspective view of the loosening member of FIG. 2 showing different types of links.
Figure 5:
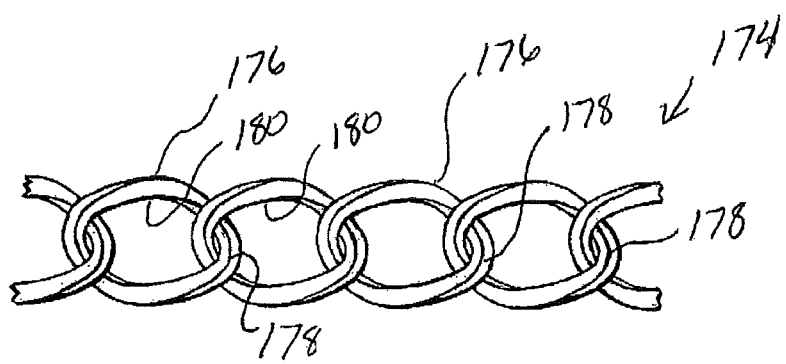
FIG. 5 depicts a partial perspective view of an alternative loosening member incorporating principles of the present invention.

The chain 132 is made from a plurality of loosening links 164 and connecting links 166 shown in FIG. 4. The loosening links 164 include a loosening edge 168 which extends above the other portions of the loosening links 164 and the connecting links 166 as seen best in FIG. 2. The loosening links 164 and the connecting links 164 define voids 170 and 172, respectively. A variety of chain configurations may be used in an apparatus incorporating principles of the present invention. By way of example, the chain 174 shown in FIG. 5 includes a plurality of links 176. Each of the links 176 are identical and include a loosening edge 178 and a void 180. The loosening edges 178 are formed in the links 176 by twisting the links 176 such that the loosening edges 178 extend above the plane in which the remaining portions of the links 170 are located. Alternatively, the chain may be fashioned such that the loosening edges are generally within the plane of the adjacent links and only extend outwardly as the chain is rotated about a pivot.

In operation, a surgical site is prepared in an acceptable manner and the cannula 106 is used to puncture a disc 182 as shown in FIG. 6. In this example, aspiration is to be used to assist in the removal of tissue. Accordingly, the tube 120 is connected to the aspiration port 114 and the tube 124 is connected between the outlet port 116 and the collector 122. Alternatively, the tube 124 may be connected to a drain or a vacuum device. Of course, the foregoing steps may be accomplished in a number of alternative variations. For example, the fluid supply components and outlet components may be connected prior to insertion of the cannula 106 into the disc 182.

Once the canula 106 is positioned in the disc 182, pressurized fluid is introduced into the tube 120. This may be accomplished by pressurizing the fluid reservoir 118 such that pressurized fluid is directed through the tube 120 and the aspiration port 114 into the tube 152. The crank handle 108 is then rotated in the clockwise direction as indicated by the arrow 184 in FIG. 6. Such rotation of the crank handle 108 causes the belt 126 to rotate in the direction of the arrows 186 in FIG. 2 causing the sprocket 128 to rotate in the direction of the arrow 188 about the pin 130.

As the sprocket 128 rotates, the arms of the sprocket 128 extend into the voids 170 and 172 of the loosening links 164 and the connecting links 166, respectively. The biasing member 148 acts upon the tensioning portion 144 thereby maintaining the chain 132 in a taut condition between the tensioning track 155 and the loosening track 135. Accordingly, the rotation of the sprocket 128 forces the chain to rotate through the feed passage 134 over the loosening track 135, through the return passage 136 and over the tensioning track 155 in the direction of the arrow 190. In alternative embodiments, a friction wheel may be used in place of a sprocket.

As the chain 132 moves in the direction of the arrow 190, the loosening edges 168 of the loosening links 166 extend into the disc 182 as the loosening track 135 presses the chain 132 into the disc 182. The loosening edges 168 thus loosen tissue within the disc 182, forming a void 192 within the disc 182 as shown in FIG. 7. If desired, the clutch 110 may be adjusted such that rotation of the crank handle 108 causes rotation of the chain 132 so long as the chain 132 is engaging tissue within the disc 182. If the chain 132 encounters a harder material, however, the increased torque will exceed the clutch setting and the sprocket 128 will no longer rotate. The clutch 110 may thus be used to reduce the potential of inadvertently damaging the surrounding vertebrae.

The loosened tissue is entrained within the voids 170 and 172 and by the loosening edges 168 and moved out of the disc 182 into the return passage 136. As the voids 170 and 172 and the loosening edges 168 rotate past the opening 154 in the tensioning track 155, the fluid passing through the tube 152 dislodges the entrained tissue out of the voids 170 and 172 and the loosening edges 168. The fluid and the dislodged tissue passes into the evacuation chamber 156 and exit the cannula 106 through the outlet port 116. The tube 124 then directs the fluid and the dislodged tissue to the collector 122.

The size of the void 192 formed in the disc 182 may be determined by comparing the volume of the fluid from the fluid reservoir 118 before and after loosening of tissue with the volume of fluid and tissue in the collector 122. Such a determination, however, may include inaccuracies due to leakage of the fluid, entrapment of fluid and/or tissue within the evacuation chamber 156, and other errors. Moreover, the volume of tissue and fluid in the collector 122 does not provide information as to the shape of the void 192. Accordingly, in one method, the tissue loosening device 100 is used to determine the volume and shape of the void 192.

Determination of the volume of the void 192 using the tissue loosening device 100 is accomplished by stopping rotation of the crank handle 108. The tissue loosening device 100 is thus in the condition depicted in FIG. 7. Specifically, the cannula 106 is located partially within the void 192. Additionally, the chain 132 is maintained in a full loop as depicted in FIG. 3 by the force exerted on the tensioning portion 144 by the biasing member 148. Thus, the indicator 158 is at the zero position of the sight glass 160.

The brake lever 112 is then moved in the direction of the arrow 194 in FIG. 7. This causes the connector arm 142 to move in the direction of the arrow 196 in FIG. 2. As the connector arm 142 moves, the locking member 138 is pivoted about the pin 140 in the direction of the arrow 198. This pivoting moves the locking member 138 from an unlocked position to a locked position as shown in FIG. 8 wherein the locking member 138 extends through a void 170 in a loosening link 164.

Movement of the chain 132 into the return passage 136 is thus precluded by the locking member 138. Moreover, movement of the chain 132 along the return passage 136 is precluded. Next, the clutch 110 is set to a measurement position wherein the torque required to activate the clutch is greater than the force exerted by the biasing member 148 against the tensioning portion 144. Then, the crank handle 108 is once again rotated in the direction of the arrow 184.

The tissue loosening device 100 is then operated in a manner similar to the tissue loosening operation described above. At this point, however, the chain 132 cannot move along the return passage 136. Accordingly, as the force applied to the chain 132 by the sprocket 128 increases above the force exerted by the biasing member 148 on the tensioning portion 144, the chain 132 presses against the tensioning track 155 and forces the tensioning portion 144 against the biasing member 148, thereby compressing the biasing member 148 and the tensioning portion 144 moves in the direction of the arrow 200 of FIG. 3.

Movement of the tensioning portion 144 in the direction of the arrow 200, thus shortening the chain travel path, allows the sprocket 128 to rotate in the direction of the arrow 188, thereby moving the chain 132 out of the feed passage 134. Because the movement of the chain 132 into the return passage 136 is constrained by the locking member 138, the chain 132 is not maintained in a taut condition across the loosening track 135. Accordingly, the chain 132 is deployed away from the loosening track 135 and deposited into the void 192.

Rotation of the crank handle 108, and thus deposition of the chain 132 within the void 192, continues until the void 192 is filled with the chain 132 as depicted in FIG. 9. When the void 192 is filled, the torque on the sprocket 128 increases rapidly. The increased torque may be detected by the operator. Alternatively, the clutch 110 may be set to disengage the sprocket 128 when the torque on the sprocket reaches a predetermined value above the force required to compress the biasing member 148. Thus, the disengagement of the sprocket may be used to signal an operator that the void 192 is filled.

Because deposition of the chain 132 requires movement of the tensioning portion 144, the movement of the tensioning portion 144 may be correlated to the amount of the chain 132 deposited into the void 192. The extent of the movement of the tensioning portion 144 may be determined by observing the position of the indicator 158 through the sight glass 160. The operator may further verify that the increased torque on the sprocket has not been caused by the full compression of the biasing member 148 against the stop 150.

The correlation of the amount of chain deposited within the void 192 with the movement of the tensioning portion 144 may be established by initially depositing the chain 132 into a graduated flask partially filled with liquid. The displacement of the liquid within the flask by the chain 132 may then be correlated to the position of the indicator 158 with respect to the gradations 162.

If desired, the chain 132 deposited within the void 192 may further be used to ascertain the shape of the void 192. Specifically, by constructing the chain 132 of a radiopaque material, a radiograph of the disc 182 with the void 192 filled with the chain 132 may be used to determine the shape of the void 192. To facilitate procedures which require the chain 132 to remain in the void 192 for extended periods, a latch (not shown) or other mechanism may be provided to lock the crank handle 108. Thus, the operator need not provide constant pressure on the crank handle 108 to counter the force exerted by the biasing member 148. Likewise, a latch (not shown) or other mechanism may be provided to secure the brake lever 112 in the locked position.

If the operator determines that additional tissue should be removed as the chain 132 is withdrawn into the cannula 106, the clutch 110 may be adjusted to allow for increased torque to be exerted on the sprocket 128. As the torque on the sprocket 128 increases, the chain 132 is pressed into the tissue defining the void 192 loosening additional tissue and the loosened tissue becomes entrained in the voids 170 and 172.

Once the chain 132 is no longer needed within the void 192, the chain 132 is withdrawn into the cannula 106. This is preferably achieved by rotating the crank handle 108 in a direction opposite to the direction indicated by the arrow 184, thereby reversing the above described process. In this manner, a controlled removal of the chain 132 is accomplished. Once the tensioning portion 144 has moved back to its original position and the chain 132 is in the tissue removal condition shown in FIG. 3, the brake lever 112 is moved in the direction of the arrow 202 of FIG. 9. This causes the locking member 138 to disengage from the chain 132, allowing additional loosening of tissue within the disc 182 by rotation of the sprocket 128 in the manner described above.

If desired, the locking member 138 may be disengaged prior to moving the tensioning portion 144 to its original position. This allows the biasing member 148 to force the tensioning portion 144 in the direction opposite to the arrow 200 in FIG. 3, thereby pulling the chain 132 out of the void 192. The rate of removal of the chain 132 may thus be established by the amount of force exerted on the tensioning portion 144 by the biasing member 148.

In either event, the sprocket 128 may be rotated such that all of the voids 170 and 172 that were within the void 192 are directed over the opening 154, allowing aspiration fluid from the tube 152 to dislodge any loosened tissue within the voids 170 and 172. In some procedures, once the desired amount of tissue has been removed, some or all of the removed tissue is subjected to a procedure such as a test or treatment. The removed tissue may then be re-inserted into the void.

A number of tissue loosening systems may be used in accordance with principles of the present invention. In alternative embodiments, the shape of the loosening track is modified to provide, for example, wider or narrower loosening areas. In further alternative embodiments, movement of the chain may be controlled using a motor which drives a sprocket or other device configured to engage a chain. The motor may be externally powered or battery powered. In some embodiments, the displacement of liquid may be determined based upon the number of rotations of the crank. Accordingly, after the locking member is engaged, the operator merely counts the revolutions of the crank. In motorized embodiments, the number of rotations may be electronically determined.

FIG. 10 depicts a portion of an alternative tissue loosening device 210. The tissue loosening device 210 is similar to the tissue loosening device 100 and includes a sprocket 212 which drives a chain 214. The main differences are that the tissue loosening device 210 includes an evacuation tube 216 and two aspiration branches 218 and 220 which are in fluid communication with an aspiration fluid supply tube 222.

In operation, a fluid supply is connected to the aspiration fluid supply tube 222. Thus, as the sprocket 212 rotates the chain 214, the chain 214 loosens tissue. The aspiration fluid is passed from the aspiration fluid supply tube 222 to the aspiration branches 218 and 220 and through the chain 214. Thus, as the chain 214 loosens tissue, the aspiration fluid passing through the aspiration branches 218 and 220 dislodges the loosened tissue from the chain 314 and the loosened tissue and aspiration fluid is directed to the evacuation tube 216. If desired, the tissue loosening device 210 may further include a tube (not shown) within the cannula 224 similar to the tube 152 for dislodging any loosened tissue which is not dislodged by the aspiration branches 218 and 220.

A variety of configurations may be used in practicing the present invention. By way of example, a cannula 224 depicted in FIG. 11 houses a loosening member 226 that extends about a loop path including a feed passage 228, a return passage 230, a loosening track 232 and a tensioning track 234. The tensioning track 234 is movable with respect to the loosening track 232 and is biased away from the loosening track 232 by a biasing member 236 which is fixedly connected at one end to a post 238 which is, in turn, fixedly connected to the cannula 224. The biasing member 236 in this embodiment is not located within the loop path. Thus, force must be used to expand the biasing member 236 when deployment of the loosening member 226 from the cannula 226 is desired.

Another configuration is depicted in the embodiment of FIG. 12 wherein the tissue loosening device 240 includes a cannula 242, a loosening member 244, a moving member 246, a freewheeling member 248 and a locking arm 250. The moving member 246 and the cannula 242 define a feed passage 252 while the freewheeling member 248 and the cannula 242 define a return passage 254. A belt 256 is used to rotate the moving member 246 about a pin 258. The freewheeling member 248 is rotated about a pin 260 by the loosening member 244.

Rotation of the loosening member 244 may be accomplished in the same manner as described with respect to the chain 132 of the embodiment of FIG. 1. The tissue loosening device 240 differs from the tissue loosening device 100 of FIG. 1 in that the loop path for the loosening member 244 is not defined by a loosening track which underlies the loosening member 244. Rather, the positioning of the moving member 246 and the freewheeling member 248 defines the shape of the loop path. Thus, various cutting widths and shapes may be provided by selection of the relative sizes and positions of the moving member 246 and the free-wheeling member 248. Additionally, in the embodiment of FIG. 12 the loosening member 244 is engaged by the locking arm 250 through the free-wheeling member 248.

Figure 13:
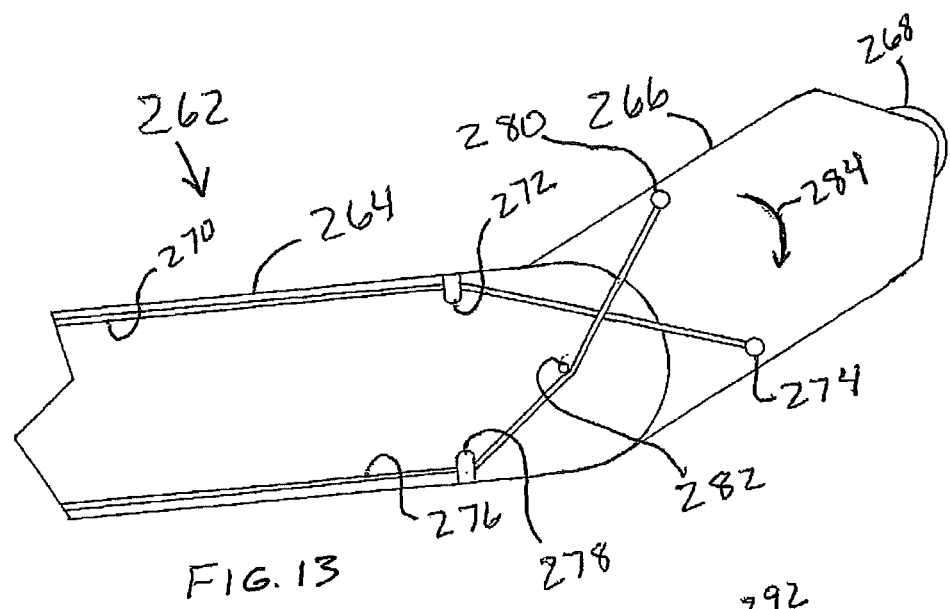
FIG. 13 depicts a partial plan view of an alternative embodiment of a cannula including a steerable tip portion in accordance with principles of the invention.
Figure 14:
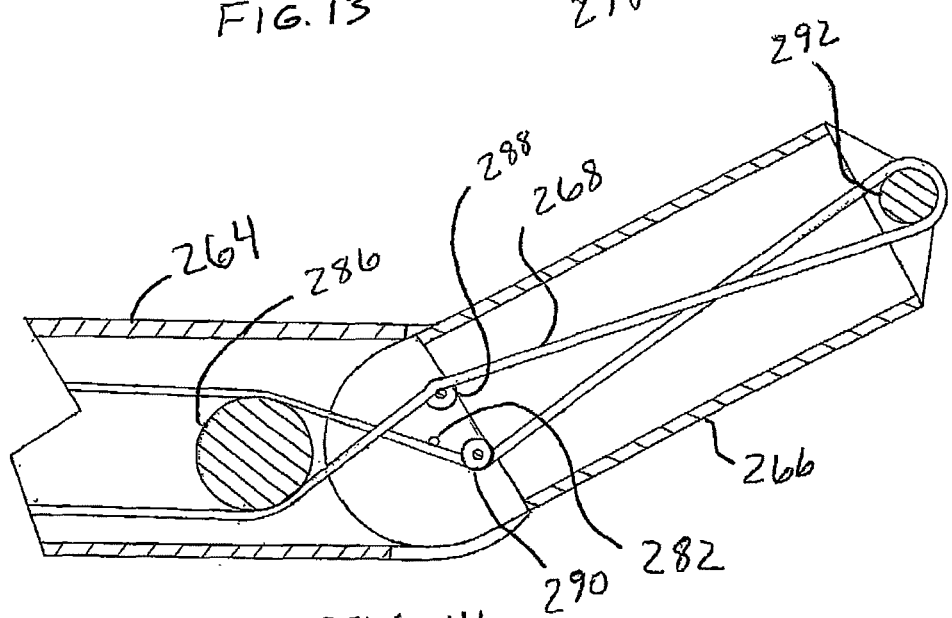
FIG. 14 depicts a partial cross-sectional view of the cannula of FIG. 13 showing the use of spacers to influence the path of a loosening member.

FIG. 13 depicts an embodiment of a loosening device which includes a pivoting cannula 262. The cannula 262 includes a base portion 264 and a pivoting tip portion 266. A loosening member 268 extends outwardly of the pivoting tip portion 266. A positioning member 270 extends through an eyelet 272 on the base portion 264 and is attached to a post 274 on the pivoting tip portion 266. A second positioning member 276 extends through an eyelet 278 on the base portion 264 and is attached to a post 280 on the pivoting tip portion 266. In the position shown in FIG. 13, the positioning member 276 is in contact with a pivot 282.

The angle of the pivoting tip portion 266 with respect to the base portion 264 is controlled by the tension applied to the positioning members 270 and 276. Specifically, by loosening the tension on the positioning member 270 and applying increased tension on the positioning member 276, the pivoting tip portion 266 rotates about the pivot 282 in the direction of the arrow 284. Alternative methods may be used to position the tip portion of a cannula including other mechanical constructs either on the outer surface of the cannula or constructs located within the cannula, and the use of shape memory metals. Additionally, a cannula may incorporate more than one pivoting portion and more than one method of controlling the pivoting of the pivoting portions.

Figure 15:
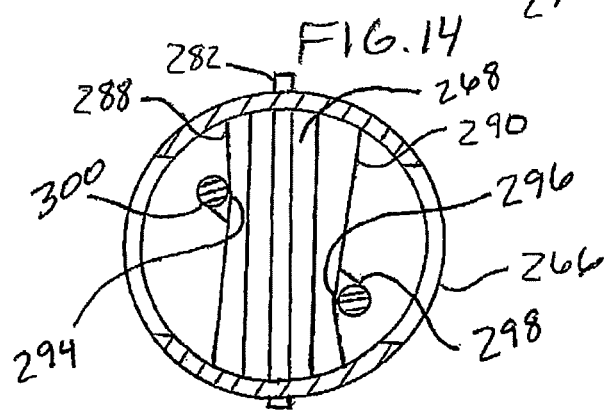
FIG. 15 depicts a cross-sectional view of the steerable tip portion of the cannula of FIG. 13 looking from the pivot pin toward the pivot and showing indentations on the spacer members that are used to influence the path of the loosening member.

In the embodiment of FIG. 13, the loop path of the loosening member 268 is defined in part by a spacer member 286 within the base portion 264, two spacer members 288 and 290 located within the pivoting tip portion 266 and an end bearing 292 which in this embodiment is a pin. The spacer members 286, 288 and 290 are used to minimize interference with the movement of the loosening member 268 from either the pivot 282 or the walls of the pivoting tip portion 266. The spacer members 286, 288 and 290 are further configured to guide the loosening member 268 so as to avoid contact of the loosening member 268 with itself as the loosening member is loosening tissue. By way of example, the spacer members 288 and 290 include grooves 294 and 296. When the loosening member 268 is placed under tension, the groove 296 urges the outgoing portion 298 downwardly within the pivoting tip portion 166 and the groove 294 urges a return portion 300 of the loosening member 268 upwardly as shown in FIG. 15.

In this embodiment, the loosening member 268 may be in the form of a segment of chain. The loosening member 268 may be provided in the form of a long length of chain. Accordingly, a segment of the chain is obtained from the supplied chain for a particular procedure and thereafter, the used segment of chain may be discarded.

In contrast to some embodiments, the embodiment of FIG. 13 does not include a sprocket or friction wheel located near the pivoting tip portion 266. Rather, the loosening member 268 is manually manipulated from the rear portion of the cannula 262. The loosening member 268 may be used to loosen tissue by pulling first on the return portion 300 and then reversing the direction of the loosening member 268 by pulling on the portion 298. Thus, the portion 300 becomes the outgoing portion and the portion 298 becomes the return portion. Additionally, the embodiment of FIG. 13 does not include a locking member. Nonetheless, the loosening member 268 may be deposited within a void by holding one of the portions 298 or 300 and pushing on the other of the portion 298 or 300.

FIG. 16 depicts an embodiment of a loosening device 310. The loosening device 310 includes a handle 312, a crank 314 and a cannula 316. A brake activator 318 extends outwardly from the handle 312. The cannula 316 includes a pivoting tip 320 and an aspiration port 322. The pivoting tip 320 is pivoted about a pivot 324 by a steering mechanism which includes a tensioning member 326 shown in FIG. 17. A loosening member 328 extends within the cannula 316 and outwardly from a bearing 330.

With reference to FIG. 18, two passages 332 and 334 within the cannula 316 are separated by a divider 336. The passages 332 and 334 are configured to complement the geometry of the individual links 338 of the loosening member 328. Thus, the loosening member 328 is maintained in a reduced profile within the passages 332 and 334. This configuration reduces the error in determining the volume of a void since the change in volume of the loosening member 328 within the passages 332 and 324, and particularly within the passage 332 when a locking mechanism is used to restrict movement of the loosening member 328 within the passage 324, is reduced. Thus, more accurate determination and compensation of the error in measurement caused by the change of volume of the loosening member within the passages 332 and 334 is possible.

In the embodiment of FIG. 18, the bearing 330 has a cross section that is larger than the width of the divider 336. Accordingly, as the links 338 approach the end of the pivoting tip 320, the links are forced outwardly, away from the longitudinal axis of the passage 332. This allows the loosening member 328 to loosen an area of tissue that is wider than the diameter of the cannula 316. Accordingly, the loosening member 328 may be used to provide aggressive loosening of tissue. Moreover, as shown in FIG. 18, there is a substantial amount of free area within the links 338 of the loosening member 328, providing a large carrying capacity for the removal of loosened tissue (T).

FIG. 19 shows a loosening member 340 within a passage 342 of a cannula 344. The loosening member 340 includes a number of links 346 with cutting edges 348. The diameter of the links 346 is closely matched with the diameter of the passage 342 as best shown in FIG. 20 which further depicts a passage 350.

The links 346 are configured in this embodiment to provide a reduced amount of loosening as the edges 348 are not as pronounced as the edges of the links 338 of FIG. 18. Additionally, there is less free area within the links 346 as evident by comparison of the links 338 in FIG. 18 with the links 346 in FIG. 19. Thus, the loosening member 340 has a more limited carrying capacity. The lack of free area also reduces the amount of "play" in the loosening member 340. Accordingly, the loosening member 340 may be preferred in embodiments wherein the loosening member will be pushed into a passage.

The configuration of FIG. 19 allows the loosening member 340 to rotate within the passages 350 and 342. The configuration shown in FIG. 21 may be used to control the manner in which a loosening member is presented to tissue to be loosened. Specifically, the cannula 352 includes two shaped passages 354 and 356. A loosening member 358 extends within the passages 354 and 356. The cross section of the passages 354 and 356 is complimentary to the footprint of the loosening member 358 within the passages 354 and 356.

Accordingly, the loosening member 358 is not free to rotate within the passages 352 or 354. Thus, the aspect of the loosening member 358 which is presented to tissue to be loosened is controlled by the shape of the passages 354 and 356 and the manner in which the loosening member is inserted into the passages 354 and 356. Therefore, the loosening member 358 may be controlled to remain in a constant orientation.

Alternatively, the loosening member 358 may be controlled to make one or more full rotations by twisting the loosening member 358 after the loosening member 358 exits the passage 354 and before the loosening member 358 is inserted into the passage 356. Rotation in less than full increments may be accomplished by rotating the orientation of one of the passages with respect to the other passage. Thus, various combinations of passage geometries, such as round, rectangular and triangular and loosening member geometries including round, rectangular and triangular may be used to provide varying degrees of control over the manner in which a particular loosening member functions.

While the present invention has been illustrated by the description of exemplary processes and system components, and while the various processes and components have been described in considerable detail, applicant does not intend to restrict or in any way limit the scope of the appended claims to such detail. Additional advantages and modifications will also readily appear to those ordinarily skilled in the art. The invention in its broadest aspects is therefore not limited to the specific details, implementations, or illustrative examples shown and described. Accordingly, departures may be made from such details without departing from the spirit or scope of applicant's general inventive concept.

We claim:

1. A method of removing intervertebral tissue, comprising:
   removing an amount of the tissue with a loosening member to form a void by rotating a continuous loop of chain links through the tissue; and loosening the tissue with a loosening edge located on at least one of the chain links;
   inserting a portion of the loosening member into the void; and
   determining the amount of the tissue removed based upon a volume defined by the portion of the loosening member inserted into the void.

2. The method of claim 1, wherein removing an amount of the tissue with a loosening member to form a void comprises:
   entraining the loosened tissue with the chain links;
   transporting the loosened tissue into a cannula with the chain links; and
   dislodging the loosened tissue from the chain links within the cannula.

3. The method of claim 1, wherein:
   inserting a portion of the loosening member into the void includes:
      engaging the continuous loop of chain links with a sprocket, and
      rotating the sprocket; and
   determining the amount of the tissue removed includes:
      determining a change in a loop path of the loop of chain links.

4. The method of claim 1, wherein inserting a portion of the loosening member into the void comprises:
   shortening a travel path of the loosening member.

5. The method of claim 4, wherein inserting a portion of the loosening member into the void comprises:
   restricting movement of the loosening member out of the void.

6. The method of claim 5, wherein restricting movement of the loosening member comprises:
   engaging a link of the loop of chain links with a locking member.

7. The method of claim 1, further comprising:
   collecting the removed tissue;
   performing a procedure on the removed tissue; and
   depositing the collected tissue in the void.

8. The method of claim 1, wherein removing an amount of the tissue comprises:
   inserting a first portion of a cannula through an incision;
   inserting a second portion of the cannula through an incision; and
   changing a position of the first portion of the cannula with respect to the second portion of the cannula.

9. A method of removing intervertebral tissue, comprising:
   removing an amount of the tissue with a loosening member to form a void by rotating a segment of chain links through the tissue in a first direction, loosening the tissue with a loosening edge located on at least a first one of the chain links, and rotating the segment of chain links through the tissue in a second direction;
   inserting a portion of the loosening member into the void; and
   determining the amount of the tissue removed based upon a volume defined by the portion of the loosening member inserted into the void.

10. The method of claim 9 wherein:
    inserting a portion of the loosening member into the void includes:
       engaging a continuous loop of the segment of chain links with a sprocket, and
       rotating the sprocket; and
    determining the amount of the tissue removed includes:
       determining the rotation of the sprocket.

11. The method of claim 9, wherein inserting a portion of the loosening member into the void comprises:
    shortening a travel path of the loosening member.

12. The method of claim 11, wherein inserting a portion of the loosening member into the void comprises:
    restricting movement of the loosening member out of the void.

13. The method of claim 12, wherein restricting movement of the loosening member comprises:
    engaging a link of the segment of chain links with a locking member.

14. The method of claim 9, wherein removing an amount of the tissue comprises:
    inserting a first portion of a cannula through an incision;
    inserting a second portion of the cannula through an incision; and
    changing a position of the first portion of the cannula with respect to the second portion of the cannula.

15. A method of removing intervertebral tissue, comprising:
    removing an amount of the tissue with a loosening member to form a void;
    inserting a portion of the loosening member into the void; and
    determining the amount of the tissue removed based upon a volume defined by the portion of the loosening member inserted into the void, wherein determining the amount of the tissue removed includes:
       determining an amount of chain links fed into a cannula.

16. The method of claim 15, wherein inserting a portion of the loosening member into the void comprises:
    shortening a travel path of the loosening member.

17. The method of claim 16, wherein inserting a portion of the loosening member into the void comprises:
    restricting movement of the loosening member out of the void.

18. The method of claim 17, wherein restricting movement of the loosening member comprises:
    engaging a link of the chain links with a locking member.

19. The method of claim 15, further comprising:
    collecting the removed tissue;
    performing a procedure on the removed tissue; and
    depositing the collected tissue in the void.

20. The method of claim 15, wherein removing an amount of the tissue comprises:
    inserting a first portion of a cannula through an incision;
    inserting a second portion of the cannula through an incision; and
    changing a position of the first portion of the cannula with respect to the second portion of the cannula.

* * * * *